(12) United States Patent
Postma et al.

(10) Patent No.: US 8,802,873 B2
(45) Date of Patent: Aug. 12, 2014

(54) PROCESS FOR THE MANUFACTURE OF EPICHLOROHYDRIN

(75) Inventors: Ron Postma, Vondelingenplaat (NL); Prasad Muppa, Vondelingenplaat (NL)

(73) Assignee: Momentive Specialty Chemicals Inc., Columbus, OH (US)

(*) Notice: Subject to any disclaimer, the term of this patent is extended or adjusted under 35 U.S.C. 154(b) by 212 days.

(21) Appl. No.: 13/056,835

(22) PCT Filed: Jul. 9, 2009

(86) PCT No.: PCT/EP2009/004976
§ 371 (c)(1),
(2), (4) Date: Jan. 31, 2011

(87) PCT Pub. No.: WO2010/012360
PCT Pub. Date: Feb. 4, 2010

(65) Prior Publication Data
US 2011/0137055 A1 Jun. 9, 2011

(30) Foreign Application Priority Data
Aug. 1, 2008 (EP) .................................. 08075681

(51) Int. Cl.
C07D 301/12 (2006.01)
B01J 21/00 (2006.01)
B01J 23/34 (2006.01)

(52) U.S. Cl.
CPC ............... *C07D 301/12* (2013.01); *B01J 23/34* (2013.01); *B01J 21/00* (2013.01)
USPC ............................. 549/531; 502/200; 502/324

(58) Field of Classification Search
CPC .......... C07D 301/12; B01J 21/00; B01J 23/34
USPC .................................. 549/531; 502/200, 324
See application file for complete search history.

(56) References Cited

U.S. PATENT DOCUMENTS

| | | |
|---|---|---|
| 4,021,454 A | 5/1977 | Wuiff et al. |
| 4,038,291 A | 7/1977 | Gipson |
| 4,127,594 A | 11/1978 | Anderson et al. |
| 4,824,976 A | 4/1989 | Clerici et al. |
| 4,937,216 A | 6/1990 | Clerici et al. |
| 4,973,718 A | 11/1990 | Buchler |
| 5,153,161 A | 10/1992 | Kershner et al. |
| 5,155,274 A | 10/1992 | Herrmann et al. |
| 5,194,416 A | 3/1993 | Jureller et al. |
| 5,256,779 A | 10/1993 | Kerschner |
| 5,274,147 A | 12/1993 | Kershner et al. |
| 5,284,944 A | 2/1994 | Madison et al. |
| 5,329,024 A | 7/1994 | Jureller et al. |
| 5,429,769 A | 7/1995 | Nicholson et al. |
| 5,466,836 A | 11/1995 | Jubin, Jr. |
| 5,516,738 A | 5/1996 | Jureller et al. |
| 5,532,389 A | 7/1996 | Trent et al. |
| 5,681,789 A | 10/1997 | Saxton et al. |
| 5,833,755 A | 11/1998 | Schlon et al. |
| 5,840,934 A | 11/1998 | Goto et al. |
| 5,973,171 A | 10/1999 | Cochran et al. |
| 6,037,484 A | 3/2000 | Grey |
| 6,054,407 A | 4/2000 | Schulz et al. |
| 6,087,513 A | 7/2000 | Liao et al. |
| 6,187,935 B1 | 2/2001 | Gosselin et al. |
| 6,288,248 B1 | 9/2001 | Strebelle |
| 6,300,506 B1 | 10/2001 | Paparatto et al. |
| 6,350,888 B1 | 2/2002 | Strebelle et al. |
| 6,380,407 B1 | 4/2002 | Catinat et al. |
| 6,500,968 B2 | 12/2002 | Zhou et al. |
| 6,500,969 B1 | 12/2002 | Zhou et al. |
| 6,541,648 B1 | 4/2003 | Paparatto et al. |
| 6,590,112 B1 | 7/2003 | Catinat et al. |
| 6,596,881 B2 | 7/2003 | Haas et al. |
| 6,596,883 B2 | 7/2003 | Hofen et al. |
| 6,624,318 B1 | 9/2003 | Muller et al. |
| 6,673,950 B1 | 1/2004 | Teles et al. |
| 6,815,552 B2 | 11/2004 | Strebelle et al. |
| 7,141,683 B2 | 11/2006 | Haas et al. |
| 7,161,000 B2 | 1/2007 | Higashimura et al. |
| 7,161,005 B2 | 1/2007 | Schlingloff et al. |
| 7,205,419 B2 | 4/2007 | Strebelle et al. |
| 7,320,779 B2 | 1/2008 | Strebelle et al. |
| 7,323,578 B2 | 1/2008 | Catinat et al. |
| 7,541,479 B1 | 6/2009 | Chang et al. |
| 7,722,847 B2 | 5/2010 | Haas et al. |
| 7,981,391 B2 | 7/2011 | Haas et al. |
| 2001/0012909 A1 | 8/2001 | Mizuno |

(Continued)

FOREIGN PATENT DOCUMENTS

| | | |
|---|---|---|
| CN | 1456582 A1 | 11/2003 |
| CN | 1900071 | 1/2007 |

(Continued)

OTHER PUBLICATIONS

De Vos et al, Tetra. Let. vol. 39 pp. 3221-3224 (1998).*
Alrich, 1998-1999 pp. 497.*
P.L. Alsters et al., "Fine-Tuning and Recycling of Homogeneous Tungstate and Polytungstate Epoxidation Catalysts", Mechanisms in Homogeneous and Heterogeneous Epoxidation Catalysis (2008) 415-428, Elsevier B.V. And Technology.
I.W.C.E. Arends et al., "Recent developments in selective catalytic epoxidations with H2O2", Topics in Catalysis, vol. 19, No. 1 (2002) 133-141.
T.H. Bennur et al., "Benzylic oxidation with H2O2 catalyzed by Mn complexes of N,N',N"-trimethyl-1,4,7-triazacyclononane: spectroscopic investigations of the active Mn Species", Journal of Molecular Catalysis A: Chemical 185 (2002) 71-80.
N.O. Brace et al., "Hydrophobic Compounds and Polymers from Long Chain Alkanamide-Formaldehyde Condensation Reactions", Journal of Organic Chemistry (1961) vol. 26, 5176-5180.

(Continued)

*Primary Examiner* — Andrew D Kosar
*Assistant Examiner* — Raymond Covington

(57) ABSTRACT

The invention relates to a process for the manufacture of epichlorohydrin ("ECH")
by catalytic oxidation of allyl chloride ("AC") with an oxidant wherein the catalytic oxidation is performed in an aqueous reaction medium, wherein a water-soluble manganese complex is used as oxidation catalyst, followed by the isolation of epichlorohydrin.

18 Claims, No Drawings

(56) References Cited

U.S. PATENT DOCUMENTS

| | | |
|---|---|---|
| 2001/0025695 A1 | 10/2001 | Patt et al. |
| 2002/0010120 A1 | 1/2002 | Hage et al. |
| 2002/0106320 A1 | 8/2002 | Zhou et al. |
| 2003/0035771 A1 | 2/2003 | Hasenzahl |
| 2003/0055293 A1 | 3/2003 | Wurziger et al. |
| 2003/0078160 A1 | 4/2003 | Hasenzahl et al. |
| 2003/0103894 A1 | 6/2003 | Hasenzahl et al. |
| 2003/0109726 A1 | 6/2003 | Balthasart |
| 2003/0144535 A1 | 7/2003 | Teles et al. |
| 2003/0158431 A1 | 8/2003 | Balthasart et al. |
| 2003/0187285 A1 | 10/2003 | Balthasart |
| 2003/0232004 A1 | 12/2003 | Zhou et al. |
| 2004/0039216 A1 | 2/2004 | Balthasart |
| 2004/0054200 A1 | 3/2004 | Paparatto et al. |
| 2004/0068128 A1 | 4/2004 | Teles et al. |
| 2004/0142843 A1 | 7/2004 | Schlingloff et al. |
| 2004/0151658 A1 | 8/2004 | Escrig et al. |
| 2004/0181081 A1 | 9/2004 | Forlin et al. |
| 2005/0065378 A1 | 3/2005 | Bosch et al. |
| 2005/0222440 A1 | 10/2005 | Khan et al. |
| 2005/0240038 A1 | 10/2005 | Gobbel et al. |
| 2005/0250955 A1 | 11/2005 | Goebbel et al. |
| 2006/0025637 A1 | 2/2006 | Babler et al. |
| 2006/0041150 A1 | 2/2006 | Catinat et al. |
| 2006/0058539 A1 | 3/2006 | Babler et al. |
| 2006/0167288 A1 | 7/2006 | Strebelle et al. |
| 2006/0216216 A1 | 9/2006 | Bassler et al. |
| 2006/0264633 A1 | 11/2006 | Schlingloff et al. |
| 2006/0277687 A1 | 12/2006 | Buhler et al. |
| 2007/0142651 A1 | 6/2007 | Le-Khac et al. |
| 2008/0103319 A1 | 5/2008 | Miller |
| 2008/0262225 A1 | 10/2008 | Schlingloff et al. |
| 2009/0029168 A1 | 1/2009 | Butters et al. |
| 2009/0068282 A1 | 3/2009 | Schlingloff et al. |
| 2009/0149666 A1 | 6/2009 | Buhler et al. |
| 2010/0029848 A1 | 2/2010 | Forlin et al. |
| 2010/0056814 A1 | 3/2010 | Chang et al. |
| 2010/0094031 A1 | 4/2010 | Trent et al. |
| 2010/0113808 A1 | 5/2010 | Liebens et al. |
| 2010/0168379 A1 | 7/2010 | Krafft et al. |
| 2010/0179300 A1 | 7/2010 | Boulos et al. |
| 2010/0180802 A1 | 7/2010 | Gumlich et al. |
| 2010/0197947 A1 | 8/2010 | Narahara et al. |
| 2010/0204494 A1 | 8/2010 | Hatano |
| 2010/0331557 A1 | 12/2010 | Strebelle et al. |
| 2011/0054197 A1 | 3/2011 | Hofen et al. |
| 2012/0130095 A1 | 5/2012 | Crampton et al. |
| 2012/0130096 A1 | 5/2012 | Crampton et al. |

FOREIGN PATENT DOCUMENTS

| | | |
|---|---|---|
| CN | 100516056 C | 7/2009 |
| CN | 101665474 B | 9/2009 |
| CN | 1931848 B | 5/2010 |
| CN | 201713456 U | 1/2011 |
| CN | 101993423 A | 3/2011 |
| CN | 101293882 B | 4/2011 |
| DE | 19923121 | 11/2000 |
| EP | 0458397 | 5/1991 |
| EP | 0458398 | 11/1991 |
| EP | 0618202 A1 | 10/1994 |
| EP | 0936219 A1 | 8/1999 |
| EP | 1115714 B1 | 5/2002 |
| EP | 1403219 | 3/2004 |
| EP | 1883730 | 2/2008 |
| EP | 2149569 A1 | 2/2010 |
| EP | 2402087 | 1/2012 |
| ES | 2336746 B1 | 1/2011 |
| JP | 2000-302766 | 10/2000 |
| JP | 2001-002662 | 1/2001 |
| JP | 2002145872 | 5/2002 |
| JP | 2005-154340 | 6/2005 |
| PL | 174464 B1 | 7/1998 |
| TW | 305831 | 6/1995 |
| TW | 200823183 | 6/2008 |
| WO | WO 99/23052 | 5/1999 |
| WO | WO 00/02872 | 10/2000 |
| WO | WO 00/76989 | 12/2000 |
| WO | WO 02/00634 | 1/2002 |
| WO | WO 03/018567 | 3/2003 |
| WO | WO 2004/028962 | 4/2004 |
| WO | WO 2004/029032 | 4/2004 |
| WO | WO 2004/048353 A1 | 6/2004 |
| WO | WO 2004/074268 | 9/2004 |
| WO | WO 2005/095370 A1 | 10/2005 |
| WO | WO 2008/098921 | 2/2007 |
| WO | WO 2007/046960 | 4/2007 |
| WO | WO 2008/078861 | 7/2008 |
| WO | WO 2008/078861 A1 | 7/2008 |
| WO | WO 2008/087657 | 7/2008 |
| WO | WO 2008/087657 A2 | 7/2008 |
| WO | WO 2009/063487 | 5/2009 |
| WO | WO 2009/063487 A2 | 5/2009 |
| WO | 100545167 C | 9/2009 |
| WO | WO 2009/129355 | 10/2009 |
| WO | WO 2010/010003 | 1/2010 |
| WO | WO 2011/032666 | 3/2011 |

OTHER PUBLICATIONS

J. Brinksma et al., "Homogeneous cis-dihydroxylation and epoxidation of olefins with high H2O2 efficiency by mixed manganese/activated carbonyl catalyst system", Tetrahedron Letters 43 (2002) 2619-2622.

A.M. d'A. Rocha Gonsalves et al, "On the mechanism of carboxylic acid co-catalyst assisted metalloporphyrin oxidations" Journal of Molecular Catalysis A: Chemical 168 (2001) 25-32.

J.W. De Boer et al., "The role of salicylic acid, L-ascorbic acid, and oxalic acid in promoting the oxidation of alkenes with H2O2 catalysed by [MnIV2(O)3(tmtacn)2]2+", Royal Society of Chemistry, Dalton Transactions (2008) 6283-6295.

J.W. De Boer, "cis-Dihydroxylation and Epoxidation of Alkenes by Manganese Catalysts Selectivity, Reactivity and Mechanism", Feb. 22, 2008, Dissertation, University of Groningen, PrintPartners Ipskamp BV, Enschede, the Netherlands.

D.E. De Vos et al., "Highly selective olefin epoxidation with manganese triazacyclononane complexes:impact of ligand substitution", Journal of Oganomettallic Chemistry 520 (1996) 195-200.

D.E. E Vos et al., "Selective Alkene Oxidation with H2O2 and a Heterogenized Mn Catalyst: Epoxidation and a New Entry to Vicinal cis-Diols", Angew. Chem. Int. Ed. 38, No. 7 (1999) 980-983.

D.E. De Vos et al., "Epoxidation of Terminal or Electron-deficient Olefins with H2O2, catalysed by Mn-trimethyltriazacyclonane Complexes in the Presence of an Oxalate Buffer", Tetrahedron Letters 39 (1998) 3221-3224.

D.E. De Vos et al., "Highly selective epoxidation of alkenes and styrenes with H2O2 and manganese complexes of the cyclic triamine 1,4,7-trimethyl-1,4,7-triazacyclononane", Chem. Commun. (1996) 917-918.

F.C. Frostick Jr. et al., "Synthesis of Some Epoxy Vinyl Monomers by Epoxidation with Peracetic Acid", by J. Am. Chem. Soc. 81 (1958) 3350-3356.

A. Grenz et al., "Synthesis and application of novel catalytically active polymers containing 1,4,7-triazacyclononanes", Chem. Commun. (2001) No. 18, 1726-1727 (Cambridge, England).

R. Hage et al., "Bleach and oxidation catalysis by manganese-1,4,7-triazacylononane complexes and hydrogen peroxide", Journal of Molecular Catalysis A: Chemical 251 (2006) 150-158.

N. Hoffman et al., "Liquid-Liquid Biphasic, Platinum-Catalyzed Hydrosilylation of AllyL Chloride with Trichlorosilane Using an Ionic Liquid Catalyst Phase in a Continuous Loop Reactor", Adv. Synth. Catal. (2008) 350, 2599-2609.

E. Kaczmarczyk et al., "Selective epoxidation of 1,4-bis(allyloxy)butane to 1-allyloxy-glycidoloxybutane in the presence of ionic liquids", Journal of Molecular Catalysis A: Chemical 265 (2007) 148-152.

E. Kaczmarczyk et al., "Epoxidation of 1,4-bis(allyloxy)butane by hydrogen peroxide using phase transfer catalysis", Journal of Molecular Catalysis A: Chemical 244 (2006) 173-178.

(56) References Cited

OTHER PUBLICATIONS

E. Kaczmarczyk et al., "Epoxidation of 1,4-diallyloxybutane to 1-allyloxy-4-glycidyloxybutane by the method of phase transfer catalysis", Journal of Molecular Catalysis A: Chemical 235 (2005) 52-56.

R. Mbeleck et al. "Stability and recycling of polymer-supported Mo(VI) alkene epoxidation catalysts", Reactive & Functional Polymers 67 (2007) 1448-1457, Elsevier Science Publishers BV, Netherlands.

A. Murphy et al., "Ligand and pH Influence on Manganese-Mediated Peracetic Acid Epoxidation of Terminal Olefins", Organic Letters, (2004) vol. 6 No. 18, 3119-3122.

L. Ningning et al., "Epoxidation of Various Functionalized Olefins by a Ti-MWW/H2O2 Catalytic System", Chin J Catal (2008) vol. 29 Issue 2, 102-104.

G.V. Nizova et al., "Hydrocarbon Oxidations with Hydrogen Peroxide Catalyzed by a Soluble Polymer-Bound Manganese(IV) Complex with 1,4,7-Triazacyclononane", Adv. Synth. Catal. (2002) 344, No. 8, 899-905.

V.C. Quee-Smith et al., "Synthesis, Structure, and Characterization of a Novel Manganese(IV) Monomer, [MnIV(Me3TACN)(OMe)3](PF6) (Me3TACN = N,N',N''-Trimethyl-1,4,7-triazacyclononane), and Its Activity toward Olefin Oxidation with Hydrogen Peroxide", Inorganic Chemistry (1996) vol. 35, No. 22, 6461-6465.

V.B. Romakh et al., "Dinuclear Manganese Complexes Containing Chiral 1,4,7-Triazacyclononane-Derived Ligands and Their Catalytic Potential for the Oxidation of Olefins, Alkanes, and Alcohols", Inorganic Chemistry (2007) vol. 46, No. 4, 1315-1331.

J.Y. Ryu et al., "Alkane Oxidation Catalyzed by Manganese-tmtacn Complexes with H2O2", Bull. Korean Chem. Soc., (2003) vol. 24, No. 12, 1835-1837.

D.C. Sherrington et al., "Polymer-Supported Mo and V Cyclohexene Epoxidation Catalysts: Activation, Activity, and Stability", Journal of Catalysis (1991) vol. 131, 115-126.

G.B. Shul'Pin et al., "Oxidations by the system 'hydrogen Peroxide-[Mn2L2O3][PF6]2 (L=1,4,7-trimethyl-1,4,7-triazacyclononane)-oxalic acid'. Part 6. Oxidation of methane and other alkanes and olefins in water", Journal of Organometallic Chemistry 690 (2005) 4498-4504.

G.B. Shul'Pin et al., "Oxidation with the 'H2O2-maganese(IV) complex-carboxylic acid' reagent", Russian Chemical Bulletin (1998) vol. 47, No. 12, 2379-2386.

K.F. Sibbons et al., "The application of manganese complexes of ligands derived from 1,4,7-triazacyclononane in oxidative catalysis" Dalton Translations (2006) 645-661, The Royal Society of Chemistry, Cambridge, England.

C. Venturello et al., "A New, Effective Catalytic System for Epoxidation of Olefins by Hydrogen Peroxide Under Phase-Transfer Conditions", Journal of Organic Chemistry (1983) vol. 48, No. 21, 3831-3833, American Chemical Society, Easton.

C.B. Woitiski et al., "Oxidations by the system 'hydrogen peroxide-dinuclear manganese(IV) complex-carboxylic acid' Part 5. Epoxidation of olefins including natural terpenes", Journal of Molecular Catalysis A: Chemical 222 (2004) 103-119.

P. Wu et al., "A novel titanosilicate with MWW structure Catalytic properties in selective epoxidation of diallyl ether with hydrogen peroxide" Journal of Catalysis 228 (2004) 183-191.

Z. Xi Et al., "An Enviromentally Benign Route for Epochlorohydrin From Allyl Chloride Epoxidation Catalyzed by Heteropolyphophatotungstate", Research on Chemical Intermediates (2007) vol. 33, No. 6, 523-534, VSP.

J.W. De Boer, "Mechanism of Cis-Dehydroxylation and Epoxidation of Alkenes by Highly H2O2 Efficient Dinuclear Managanese Catalysts." with Online Supporting Information, Inorganic Chemistry (2007), vol. 46, No. 16, pp. 6353-6372, American Chemical Society.

* cited by examiner

PROCESS FOR THE MANUFACTURE OF EPICHLOROHYDRIN

RELATED APPLICATION DATA

This application claims the benefit of PCT Application PCT/EP2009/004976 with an International Filing Date of Jul. 9, 2009, published as WO 2010/012360, which PCT Application PCT/EP2009/004976 further claims priority to European Patent Application No. EP08075681.0 filed Aug. 1, 2008, the entire contents of both are hereby incorporated by reference.

TECHNICAL FIELD

The invention relates to a process for the manufacture of epichlorohydrin ("ECH") by catalytic oxidation of allyl chloride ("AC") using hydrogen peroxide and a manganese complex.

BACKGROUND ART

ECH (also known as "EPI") is of particular interest. It is for instance used as a building block in the manufacture of plastics, epoxy resins, phenoxy resins and other polymers. It has been used as a solvent for cellulose, resins and paints and it has found use as an insect fumigant. ECH may react with water, forming the corresponding diol.

Conventional ECH production routes involve the use of chloride containing oxidants, such as HOCl. This method suffers a.o. from a relatively large amount of co-produced chloride salts.

Despite the strong interest in ECH, a high atom-efficient production route without the coproduction of salts and/or other byproducts is not yet available. Moreover, alternative preparation methods suffer from side reactions and/or isolation problems. The ECH typically has to undergo various purification steps before it can be used for subsequent reactions.

For instance, the process for the manufacture of ECH in WO2004/048353 is carried out in a reaction medium comprising at least 75% w of organic material, causing significant isolation problems. Moreover, it is known from this reference and other references wherein ECH is made that the product of such processes frequently comprises both epichlorohydrin and the various byproducts resulting from the opening of the oxirane ring, namely 1-chloro-3-methoxy-2-propanol, 1-chloro-2-methoxy-3-propanol, 3-chloro-1,3-propanediol and 1,3-dichloro-2-propanol.

From the above it is clear the industry is still looking for a commercially feasible process for the manufacture of ECH, in high turnover numbers and at high selectivity, meaning free of byproducts such as diols. This process should also allow the use of an aqueous solvent as reaction medium, to avoid environmental and other problems related to acetonitrile and similar organic solvents. The present invention overcomes these disadvantages.

DISCLOSURE OF THE INVENTION

Accordingly, the invention provides a process for the manufacture of epichlorohydrin ("ECH")
  by catalytic oxidation of allyl chloride ("AC") with an oxidant wherein the catalytic oxidation is performed in an aqueous reaction medium, wherein a water-soluble manganese complex is used as oxidation catalyst, followed by the isolation of epichlorohydrin.

In a preferred embodiment, the ECH or part of the ECH is isolated as an organic phase, which phase comprises ECH or a mixture of allyl chloride and ECH. Moreover, there may be two organic phases with differing amounts of AC and ECH and hence different densities.

Mode(s) For Carrying Out The Invention

As used in the current specification, the expressions epoxidation and oxidation refer to the same reaction; the conversion of the carbon-carbon double bond of the allyl chloride into an oxirane ring. The invention is hereafter discussed in greater detail.

It is rather surprising that the current process can be used to prepare ECH at high selectivity with no noticeable amounts of byproducts (diols and such), despite having the reaction performed in an aqueous reaction medium.

In terms of water-soluble manganese complexes that may be used as oxidation catalyst, many suitable complexes are known. Note in this respect that what is described in this patent is actually the catalyst precursor. Indeed, in all open and patent literature typically a catalyst precursor is defined, as the active species during the system may be different and in fact even changing during the reaction that it catalyses. For convenience sake, and as this is common in the literature, we refer to the complex as if it is the catalyst.

Typically the catalyst comprises a manganese atom or a number of manganese atoms coordinated with a ligand or ligands. The manganese atom(s) may be in a II, III or IV oxidation state and be activated during the reaction. Of particular interest are binuclear manganese complexes. Suitable manganese complexes therefore include mononuclear species of the general formula (I):

[LMnX$_3$]Y          (I)

and binuclear species of the general formula (II):

[LMn(μ-X)$_3$MnL]Y$_2$          (II)

wherein Mn is a manganese; L or each L independently is a polydentate ligand, preferably a cyclic or acyclic compound containing 3 nitrogen atoms; each X independently is a coordinating species and each μ–X independently is a bridging coordinating species, selected from the group consisting of: RO$^-$, Cl$^-$, Br$^-$, I$^-$, NCS$^-$, N$_3^-$, I$_3^-$, NH$_3$, NR$_3$, RCOO$^-$, RSO$_3^-$, RSO$_4^-$, OH$^-$, O$^{2-}$, O$_2^{2-}$, HOO$^-$, H$_2$O, SH$^-$, CN$^-$, OCN$^-$, and S$_4^{2-}$ and combinations thereof, wherein R is a C$_1$-C$_{20}$ radical selected from the group consisting of alkyl, cycloalkyl, aryl, benzyl and combinations thereof, and Y is an oxidatively-stable counterion. Counterion Y may for instance be an anion selected from the group consisting of RO$^-$, Cl$^-$, Br$^-$, I$^-$, F$^-$, SO$_4^{2-}$, RCOO$^-$, PF$_6^-$, acetate, tosylate, triflate (CF$_3$SO$_3^-$) and a combination thereof with R once again being a C$_1$ to C$_{20}$ radical selected from the group consisting of alkyl, cycloalkyl, aryl, benzyl and combination thereof. The type of anion is not very critical, although some anions are more preferred than others. A preferred counterion is PF$_6^-$. Ligands which are suitable for the present invention are acyclic compounds containing at least 7 atoms in the backbone or cyclic compounds containing at least 9 atoms in the ring, each having the nitrogen atoms separated by at least two carbon atoms. A preferred class of ligands is that based on (substituted) triazacyclononane ("Tacn"). The prefer ligand is 1,4,7-trimethyl-1,4,7,-triazacyclononane ("TmTacn"), which is commercially available from for instance Aldrich. In this respect it is important to note that the water-solubility of the manganese catalyst is a function of all the aforementioned catalyst components. For instance, a mononuclear manganese complex prepared from $MnSO_4$ and TmTacn was found to be insufficiently soluble.

Dinuclear manganese complexes are preferred, because of their greater activity and solubility in water. Preferred dinuclear manganese complexes are those of the formula $[Mn^{IV}_2(\mu-O)_3L_2]Y_2$, wherein L and Y have the meaning identified above, preferably TmTacn as ligand, and $PF_6^-$ as counterion.

According to the present invention, the manganese complex may be utilized directly or as adsorbed onto a solvent insoluble support surface. Illustrative but nonlimiting examples of such substrates are structured aluminosilicates (e.g. Zeolite A, faujasite and sodalite), amorphous aluminosilicates, silica, alumina, charcoal, microporous polymeric resins (e.g. polystyrene beads formed through high internal phase emulsion technology) and clays (especially layered clays such as hectorite and hydrotalcite). Relative weight ratios of the manganese complex to the support may range anywhere from about 10:1 to about 1:10,000.

The manganese complex is used in catalytically effective amounts. Typically, the catalyst is used in a molar ratio of catalyst (Mn) versus allyl chloride of from 1:10 to 1:10,000,000, preferably of from 1:20 to 1:100,000, most preferably of from 1:50 to 1:1000. As a matter of convenience the amount of catalyst may also be expressed in terms of its concentration, when keeping in mind the volume of the aqueous medium. For instance, it may be used in a molar concentration (based on the Mn) of from 0.001 to 10 mmol, preferred of from 0.01 to 7 mmol and most preferably of from 0.01 to 2 mmol. In this respect it is also important to note that the epoxidation is first order on the catalyst concentration and proportional to the catalyst amount. With increase in the catalyst amount, the activity increases. The higher amounts, however, need to be balanced by the higher cost.

An advantage of the current invention, using a water soluble manganese complex is that the catalyst essentially does not migrate to the organic phase.

The aqueous reaction medium typically is a water phase containing AC and/or ECH and less than 25% by volume, preferably only minor amounts, if any, of other organic compounds. Although not preferred, the reaction medium may contain minor amounts of co-solvents such as methanol and acetone and the like. Whilst excluding the presence of AC and/or ECH, the aqueous reaction medium therefore suitably comprises at least 90% by volume of water, preferably 95% v, more preferably 99% v, still more preferably 99.9% v of water. Most preferably, however, the aqueous reaction medium (again, excluding any AC and/or ECH dissolved therein) is essentially a 100% water phase.

The aqueous reaction medium may contain a buffer system so as to stabilize the pH. For instance, it has been found that the aqueous reaction medium is suitably stabilized in a pH range of 2.5 to 8, whereas the preferred pH range is between 3 and 7 and the most preferred is between 3.5 to 6.5. The pH is therefore (well) below that used when bleaching olefins, typically carried out at more alkaline conditions (e.g., pH adjusted with $NaHCO_3$ to 9.0). The suitable or preferred range may be achieved by several known acid-salt combinations, with the preferred combination being based on oxalic acid-oxalate salt, or acetate acid-acetate salt. When oxalic acid and sodium oxalate are used, the pH ratio may be varied from 3.7 to 4.2. Typically, this buffer may be used in a molar ratio to the catalyst of about 10:1, but the amounts may be varied broadly, e.g., ranging from 1:1 to 100:1.

The aqueous reaction medium may also contain a phase transfer agent and/or a surfactant. Known phase transfer agents that may be used in the process of the invention include quaternary alkyl ammonium salts. Known surfactants that may be used in the process of the invention include non ionic surfactants such as Triton X100™ available from Union Carbide.

It is believed to be beneficial that the aqueous reaction medium contains at least trace amounts of allyl chloride. Although this is purely a hypothesis, it is believed that the presence of allyl chloride allows the catalyst to remain active, whereas it is believed that without the presence of allyl chloride and/or due to the presence of ECH and/or oxidant without allyl chloride present the activity of the active catalyst reduces.

The reaction conditions for the catalytic oxidation may be quickly determined by a person skilled in the art. Pressure is not of particular relevance. The reaction is believed to be exothermic, and cooling of the reaction medium may be required. The reaction is preferably carried out at temperatures anywhere from −5° C. to 30° C., preferably from 0° C. to 20° C., and most preferably from 0° C. to 10° C.

It is noted that the reaction product ECH, is present in very small amounts in the aqueous phase. Instead, ECH forms an organic phase, together with the (surplus of) allyl chloride, if present. Of particular interest in the process of the current invention is that the reaction product, ECH, can form a separate phase. Thus, by proper selection of the reaction conditions, catalytically effective amount of a water-soluble manganese complex as epoxidation catalyst and an aqueous reaction medium, it has been found that allyl chloride is converted into ECH which then separates from the aqueous reaction medium due to its limited solubility, forming a product layer or product layers comprising ECH that is/are free of any byproducts and free of any organic solvents. The ECH product layer may contain some unreacted allyl chloride dissolved therein. As a matter of fact, there may be two product layers, differing in concentration of allyl chloride and ECH which therefore may have a density greater or smaller than the density of the aqueous reaction medium.

To achieve the high selectivity and turnover numbers of the current invention, the allyl chloride and oxidant are preferably reacted at a molar ratio of from 1:0.1 to 1:10, more preferably of from 1:0.2 to 1:1.2, still more preferably of from 1:0.8 to 1:1. Allyl chloride is preferably used in equimolar excess of oxidant. The amount of reactants should be such that at full conversion of the allyl chloride more ECH is produced than is soluble in the aqueous reaction medium. Preferably, the amount of reactants is such at that 80% conversion of the allyl chloride more ECH is produced than is soluble in the aqueous reaction medium. More preferably, the amount of reactants is such at that 50% conversion of the allyl chloride more ECH is produced than is soluble in the aqueous reaction medium. This process results in the production of ECH at high turnover numbers, with high selectivity towards ECH with moreover improved ease of isolating the ECH. To ensure optimal results, the addition of reactants should be to the aqueous medium and not to the organic phase, should that have formed during the reaction.

As mentioned before, it is believed beneficial to have some allyl chloride present in the aqueous reaction medium. Mixing an organic phase, if present, rich in allyl chloride with the aqueous phase may be beneficial, whereas back-mixing an organic phase purely composed of ECH should preferably be avoided. Thus, it is believed that mixing or stirring improves the conversion of allyl chloride into ECH, but that ECH itself retards the conversion of allyl chloride.

The conversion of allyl chloride ("AC") into epichlorohydrin is discussed hereinafter. Depending on the reaction conditions, the reaction may be performed in a three layer system comprising an organic phase at the bottom, and an organic phase on top. The phase at the bottom may have a higher density then the reaction medium, for instance caused by a relatively high ECH content, whereas the organic phase on top will have lower density then the reaction medium, for instance caused by a relatively high AC content. Subject to a.o. the stirring conditions, however, it may not be immediately apparent that such separate phases exist or are being created during the reaction; for instance the separate phase(s) may be observed only after the system has been in rest. The catalytic oxidation of the present invention is carried out preferably using hydrogen peroxide as oxidant. Other oxidants may be used, i.e. as precursor to the hydrogen peroxide, but given the availability and to reduce environmental impact hydrogen peroxide is the preferred oxidant. Hydrogen peroxide has strong oxidizing properties. As bleaching agent it is mostly used for bleaching paper. It is typically used in an aqueous solution. The concentration of hydrogen peroxide may vary, from 15% (e.g., consumer grade for bleaching hair) to 98% (propellant grade), with a preference for industrial grades varying from 20 to 60%, preferably from 30 to 50%.

To ensure optimal oxidant efficiency, the oxidant is preferably added to the aqueous reaction medium at a rate about equal to the reaction rate of the catalytic oxidation.

The catalytic oxidation may be performed in a batch process, in a continuous process or in a semi-continuous process. Indeed, the process may be modified in various aspects without departing from the gist of the invention.

By way of general example the catalytic oxidation of allyl chloride is described hereafter.

The catalytic oxidation may be performed in a common stirred tank reactor provided with a means of stirring. For instance, this may be a common blade agitator operating under an agitation speed of around 250 rpm. The catalyst, aqueous reaction medium and reactants may be added in batch, or the reactants may be added over a period of time. If hydrogen peroxide is added during the reaction, then it is added to either the (stirred) organic phase comprising the allyl chloride or the (stirred) aqueous reaction medium.

In (semi)continuous operations, various recycling streams may be used to control the reaction conditions (maintained at a temperature of between −5° C. and 10° C.) and to optimize the production rate.

In terms of process design, a settler may be added to optimize the gravitational separation of the ECH. Likewise, a membrane unit may be used to recycle the aqueous reaction medium with reduced loss of catalyst.

On example of a mass balance for the reaction process according to the invention is:

| ECH | about 11 000 kg/h |
|---|---|
| AC | about 9 100 kg/h |
| $H_2O_2$ (35%) | about 6 457 kg/h |
| $H_2O$ | about 2 140 kg/h |

As a result of this mass balance, the ratio ECH/cat is about 8000 mol/mol.

The following examples will more fully illustrate selected embodiments of this invention. All parts, percentages and proportions referred to herein and in the appended claims are by weight unless otherwise indicated.

EXAMPLES

Example 1

The catalytic oxidation was carried out with a catalyst of the formula:

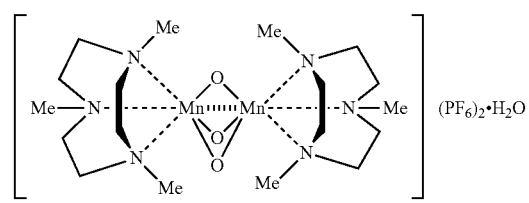

Also used is an oxalate/oxalic acid buffer, with 35% aqueous $H_2O_2$ as oxidant, and water as aqueous reaction medium. The experiment is carried out with allyl chloride as the terminal olefin.

Experimental:

In a typical epoxidation reaction 9.3 µmol of catalyst in 50 mL of water, 112.5 µmol of sodium oxalate in 7.5 mL of $H_2O$ and 112.5 µmol of oxalic acid in 7.5 mL of $H_2O$ were taken into a three-neck round-bottomed flask equipped with a mechanical stirrer. The reaction started with the addition of olefin (150 mmol) and dilute $H_2O_2$ (200 mmol) at 4° C.

10 mL of extra water was added as solvent for the reaction. The oxidant was added under flow conditions with 8.8 mL/hr into the reaction solution. The pH of the reaction solution was 3.5 to 3.6 and the stirring rate was maintained at 210 rpm for the most of the experiments with mechanical stirrer.

Results and Discussion

The manganese complex produced ECH efficiently using water as solvent. During the epoxidation using water as solvent, at the beginning of the reaction, AC was present as a separate layer on top of the aqueous catalyst solution. As the epoxidation progressed the ECH was formed in a separate phase along with some AC dissolved in it. The reaction was performed several times. On occasion the system formed three phases from top to bottom: an organic, an aqueous and a second organic phase. At the end of the reaction both the top and bottom organic phases comprised major amounts of ECH and AC. Minor amounts of AC and ECH were also found in the aqueous phase. On the other hand, the system has also resulted in a two layer system, with an organic phase (comprising AC and ECH), and an aqueous phase.

This example provided a 50% yield of ECH based on allyl chloride, produced at 40% selectivity of hydrogen peroxide, with 7800 TON. There were no noticeable amounts of diols or other side products produced.

Example 2

Various experiments were carried out in the manner of Example 1. In Table 1 the results of the epoxidation of AC at various stirring rates are presented.

TABLE 1

Epoxidation of AC: Variation of stirring rate

| No. | Time period (h) | Stirring rate (rpm) | ECH (mmol) | TON (for ECH) |
|---|---|---|---|---|
| 1 | 6 | 650 | 33 | 3500 |
| 2 | 6 | 500 | 36 | 3900 |
| 3 | 6 | 210 | 73 | 7800 |
| 4 | 4 | 210 | 64 | 6900 |
| 5 | 4 | 100 | 37 | 3900 |

This example illustrates that the yield of ECH increases with the stirring rate until an optimum has been reached.

Example 3

Variation in Catalyst Amount

The rate of the production of ECH was proportional to the concentration of the catalyst. This example illustrates that increased amounts of catalyst leads to increased production of ECH.

TABLE 2

Epoxidation of AC: Variation of catalyst amount

| No. | Time period (h) | Catalyst amount (µmol) | Efficiency peroxide (%) | ECH (mmol) | TON |
|---|---|---|---|---|---|
| 1 | 4 | 4.7 | 30 | 30 | 6400 |
| 2 | 4 | 9.4 | 42 | 64 | 6900 |
| 3 | 4 | 18.3 | 46 | 66 | 3600 |

Example 4

Effect of pH

In the previous experiments the epoxidation reactions have been performed at low pH around 3.5 to 3.6. Here we show that the catalyst was active in both acidic and basic conditions, that is at pH=2.6 with only oxalic acid present, as well as at pH=8 with only sodium oxalate. These results give evidence that the catalyst system was active in the wide pH range for AC epoxidation.

TABLE 2

Effect pH for epoxidation of allyl chloride

| No. | pH | peroxide consumed (mmol) | mmol of ECH formed in Organic phase | in Aqueous phase | TON ECH | Selectivity of peroxide (%) |
|---|---|---|---|---|---|---|
| 1 | 2.6 | 55 | 15.4 | 7.6 | 2400 | 42 |
| 2 | 8 | 121 | 29 | 19 | 5000 | 39 |

The invention claimed is:

1. A process for the manufacture of epichlorohydrin, comprising:
reacting allyl chloride with an oxidant in the presence of a catalyst in an aqueous reaction medium, wherein the catalyst comprises a water-soluble manganese complex and the molar ratio of allyl chloride to oxidant is from 1:0.1 to 1:1; and isolating an epichlorohydrin product, wherein the water-soluble manganese complex comprises a mononuclear manganese complex of the general formula (I):

[LMnX$_3$]Y  (I)

or a binuclear manganese complex of the general formula (II):

[LMn(µ-X)$_3$MnL]Y$_2$  (II)

wherein Mn is a manganese; L or each L independently is a polydentate ligand; each X independently is a coordinating species: and each µ-X independently is a bridging coordinating species, selected from the group consisting of: RO$^-$, Cl$^-$, Br$^{31}$, I$^-$, F$^-$, NCS$^-$, N$_3^-$, I$_3^-$, NH$_3$, NR$_3$, RCOO$^-$, RSO$_3^-$, RSO$_4^-$, OH$^-$, O$^{2-}$, O$_2^{2-}$, HOO$^-$, H$_2$O, SH$^-$, CN$^-$, OCN$^-$, and S4$^{2-}$ and combinations thereof, wherein R is a C$_1$-C$_{20}$ radical selected from the group consisting of alkyl, cycloalkyl, aryl, benzyl and combinations thereof, and Y is an oxidatively-stable counterion.

2. The process of claim 1, wherein the epichlorohydrin product or a part of the epichlorohydrin product is isolated as an organic phase, wherein the organic phase comprises epichlorohydrin product or a mixture of allyl chloride and epichlorohydrin product.

3. The process of claim 1, wherein each polydentate ligand is independently selected from acyclic compounds containing at least 7 atoms in the backbone or cyclic compounds containing at least 9 atoms in the ring, wherein each polydentate ligand having 3 nitrogen atoms with the nitrogen atoms separated by at least two carbon atoms.

4. The process of claim 1, wherein a binuclear water-soluble manganese complex is used as the catalyst.

5. The process of claim 1, wherein the catalyst is used in a molar ratio of the catalyst (Mn) to the allyl chloride from 1:10 to 1:10,000,000.

6. The process of claim 1, wherein the aqueous reaction medium is a water phase.

7. The process of claim 1, wherein the aqueous reaction medium further comprises a buffer system and a pH in the range of from 2.5 to 7.

8. The process of claim 1, wherein the reaction is carried out at temperatures in the range from −5° C. and 30° C.

9. The process of claim 1, wherein the oxidant is hydrogen peroxide.

10. The process of claim 9, wherein the hydrogen peroxide is used as an aqueous solution in a concentration from 15% to 98%.

11. The process of claim 1, wherein the allyl chloride and the oxidant are reacted at a molar ratio of the allyl chloride to the oxidant in the range from 1:0.2 to 0.8.

12. The process of claim 1, wherein the oxidant is added to the aqueous reaction medium at a rate about equal to the reaction rate.

13. The process of claim 1, wherein the reaction is performed in a batch process, in a continuous process or in a semi-continuous process.

14. The process of claim 1, wherein the aqueous reaction medium comprises a 100% aqueous medium excluding any dissolved epoxide and ally chloride.

15. The process of claim 1, wherein the wherein each L is independently a triazacyclononane or substituted triazacyclononane.

16. The process of claim 1, wherein the manganese complex comprises the formula [Mn$^{IV}_2$(µ-O)$_3$L$_2$]Y$_2$, wherein L is a triazacyclononane or substituted triazacyclononane and the counterion Y is PF$_6^-$ or CH$_3$CO$_2^-$.

17. The process of claim 1, wherein the catalyst comprises a mononuclear manganese complex of the general formula (I):

[LMnX$_3$]Y  (I)

or a binuclear manganese complex of the general formula (II):

[LMn(µ-X)$_3$MnL]Y$_2$  (II)

wherein Mn is a manganese; L or each L independently is a polydentate ligand; each X independently is a coordinating species and each µ-X independently is a bridging coordinating species, selected from the group consisting of: RO$^-$, Cl$^-$, Br$^-$, I$^-$, F$^-$, NCS$^-$, N$_3^-$, I$_3^-$, NH$_3$, NR$_3$, RCOO$^-$, RSO$_3^{31}$, RSO$_4^-$, OH$^-$, O$^{2-}$, O$_2^{2-}$, HOO$^-$, H$_2$O, SH$^-$, CN$^-$, OCN$^-$, and S$_4^{2-}$ and combinations thereof, wherein R is a C$_1$-C$_{20}$ radical selected from the group consisting of alkyl, cycloalkyl, aryl, benzyl and combinations thereof, and Y is an oxidatively-stable counterion;

wherein the aqueous reaction medium further comprises a buffer system with a pH range from 2.5 to 7; and wherein the molar ratio of the terminal olefin to the hydrogen peroxide in the range of from 1:0.1 to 1.2:1.

18. The process of claim 1, wherein Y is an oxidatively-stable counterion selected from the group consisting of $RO^-$, $Cl^-$, $Br^-$, $I^-$, $F^-$, $SO_4^{2-}$, $RCOO^-$, $PF_6^-$, acetate, tosylate, triflate ($CF_3SO_3^-$) and a combination thereof.

* * * * *